United States Patent [19]

Yoshioka et al.

[11] 4,122,078

[45] Oct. 24, 1978

[54] ANTIGENS AND ANTIBODIES OF CATECHOLAMINES

[75] Inventors: Masanori Yoshioka, Tokyo; Akira Miwa, Chiba; Zenzo Tamura, Tokyo, all of Japan

[73] Assignee: Daiichi Seiyaku Co., Ltd., Tokyo, Japan

[21] Appl. No.: 659,588

[22] Filed: Feb. 19, 1976

[30] Foreign Application Priority Data

Feb. 28, 1975 [JP] Japan ................... 50-24605

[51] Int. Cl.$^2$ .............................................. C07G 7/00
[52] U.S. Cl. ................. 260/121; 260/112 B; 260/112 R; 424/1; 424/12; 424/85; 424/88
[58] Field of Search ............... 260/112 R, 112 B, 121, 260/78 A; 424/85, 88

[56] References Cited

U.S. PATENT DOCUMENTS

| 3,690,834 | 9/1972 | Goldstein et al. | 23/230 R |
| 3,704,282 | 11/1972 | Spector | 260/112 X |
| 3,852,157 | 12/1974 | Rubenstein et al. | 195/63 |
| 3,996,344 | 12/1976 | Gross | 260/112 R |
| 4,016,146 | 4/1977 | Soares | 260/112 R |

OTHER PUBLICATIONS

Chem. Pharm. Bull. 24, (1976), pp. 1422-1424, Miwa et al.
Organic Chemistry, 3rd Ed. (1970) Hendrickson et al., p. 1075.
Nature, 207, pp. 1155-1157 (1965), Bariana et al.
J. Biol. Chem. 174, pp. 827-843, (1948), Fraenkel-Conrat et al.
J. Am. Chem. Soc. 68, pp. 1894-1901 (1946), Burckhalter et al.
Science, vol. 176, 1972, pp. 1143-1144, Wainer et al.
J. of Medicinal Chem., vol. 19, 1976, pp. 20-25, Faraj et al.
Ann. N.Y. Academy of Science, 181 (1971), pp. 181-202, Sela.

Primary Examiner—Howard E. Schain
Attorney, Agent, or Firm—Oblon, Fisher, Spivak, McClelland & Maier

[57] ABSTRACT

An antigen consisting essentially of a catecholamine and a protein of polypeptide, wherein the protein or polypeptide is bonded to the phenyl nucleus of the catecholamine.

6 Claims, No Drawings

ANTIGENS AND ANTIBODIES OF CATECHOLAMINES

BACKGROUND OF THE INVENTION

Hapten radioimmunoassay is known to be useful for the measurement of small components in the living body, especially steroid hormones. However, there are very few reports in the literature concerning the assay of such a small molecules as catecholamines.

Went et al reported that adrenaline antigen was prepared by coupling diazoadrenaline with a serum albumin under at alkaline conditions. Since catecholamines are unstable under alkaline condition in the presence of oxygen, the antigen may be structurally changed at the catechol portion, so the antibodies produced therefrom may not be specific for adrenaline (Arch. Exp. Path. Pharm. 193 page 609 (1939)).

Spector disclosed the synthesis of catecholamine antigens by conjugating a catecholamine with a protein or polypeptide in the presence of a carbodiimide by a peptide linkage (U.S. Pat. No. 3,704,282). While the amino group of the catecholamine is utilized in the peptide linkage, such amino group of the catecholamine should be maintained as free form in the conjugate for the production of the specific antibody.

Therefore, these antigens previously reported are not satisfactory for the production of the specific catecholamine antibodies.

Summary of the Invention

This invention relates to novel type of antigens of catecholamines, and to antibodies produced therefrom.

In this specification and claims, the catecholamines used as haptens mean the compounds having catechol moiety and an amino group, which can be represented by the general formula,

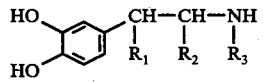

wherein $R_1, R_2$ and $R_3$ each represent $H, OH, CH_3$ or $COOH$. The compounds of the above formula include, for example, epinephrine ($R_1=OH, R_2=H, R_3=CH_3$), norepinephrine($R_1=OH, R_2=H, R_3=H$), dopamine($R_1=H, R_2=H, R_3=H$) and dopa($R_1=H, R_2=COOH, R_3=H$).

The antigens of this invention are the conjugates of catecholamines with carrier materials, in which the conjugation bond is attached to a certain position of the phenyl nucleus of catecholamine, so that all the characteristic groups of the catecholamine molecule for the production of the specific antibody survive to effect. Therefore, the present antibodies produced by the injection of these conjugates to host animals have high specificities to the antigens (haptens and conjugates).

The procedure for preparing the conjugates of this invention is summarized by the following reaction sequence.

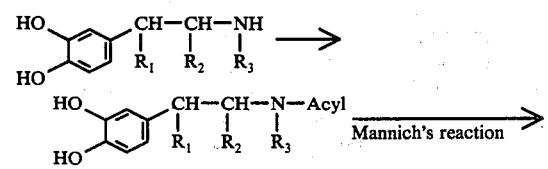

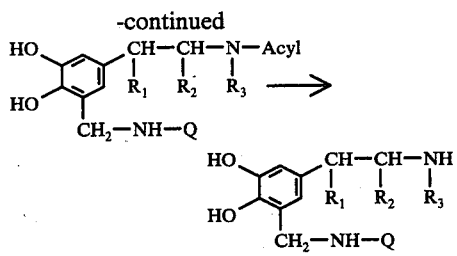

Wherein $R_1, R_2$ and $R_3$ are the same as above and —NH—Q means a carrier material.

DETAILED DESCRIPTION OF THE INVENTION

The techniques utilized in the synthesis of the conjugate are well-known in the art except for the type of protective groups. In this method, the amino group of the catecholamine is protected by an acyl group, and the conjugation between the protected catechloamine and a carrier material is carried out by the Mannich reaction, then the protective group is removed.

As for the carrier material, mammalian serum proteins or polypeptides can be used. Examples of the serum proteins include mammalian serum albumin and gamma globulin and out of these, usually bovine serum albumin(BSA) or rabbit serum albumin(RSA) is used. The polypeptides mean for example, polylysine or polyglutamic acid.

For the protective purpose of amino group, acyl groups are generally useful, however, maleyl group, trifluoroacetyl group and citraconyl group are most useful to protect catecholamines, because the acylation with these selected acyl groups may be easily performed and they can be smoothly removed by hydrolysing under mild conditions. The acylation is carried out using several fold moles, preferably 2-fold moles, of maleic anhydride, trifluoroacetic acid or citraconic anhydride to catecholamine in a suitable solvent such as methanol, dimethylformamide and the like. The reaction proceeds at room temperature or at slightly elevated temperature. After removing the excess acylating agent, the reaction mixture is neutralized with diluted sodium hydroxide, sodium bicarbonate and the product was the like. Then, the unreacted catecholamine is removed, if necessary, with a cation exchange resin(Na type) and product is lyophilized. The protected catecholamine may be stored as the lyophile, however, it can be preferably stocked after the following treatment. The lyophilized intermediate is dissolved in a small amount of methanol and precipitated by the addition of ethyl acetate and then the precipitate is collected by centrifuging and dried under reduced pressure.

The physical properties of the protected catecholamines were determined by electrophoresis on a cellulose-acetate and thin layer chromatography on silica gel or cellulose. The conditions and results are summarized below.

Electrophosesis on cellulose-acetate

| | |
|---|---|
| Condition: | Buffer solution;0.07M Veronal-sodium Veronal, pH 8.6 |
| | Electric current and voltage; 2mA/cm, 200–250volt |
| | Temperature and time; 10–15° C, 15 minutes |
| Results: | N-maleyldopa 1.53 |
| | N-maleylepinephrine 0.68 |
| | N-maleylnorepinephrine 0.71 |

-continued

| | |
|---|---|
| N-maleyldopamine | 0.71 |

All the maleyl compounds moved to the direction of anode, and the results were represented by the relative mobility to bromocresolgreen (1.0) standard, and in the procedure, the spots were detected by the color reaction with ferrous sulfate (J. R. Doty, Analytical Chemistry 20,1166(1948)). Starting materials (catecholamines) moved to the direction of cathode.

Thin layer chromatography (No. 1)

| Condition: | Carrier; silica gel |
|---|---|
| | Solvent; methanol-acetic acid (100:1) |
| | Temperature and time; 10–15° C, 20 minutes |
| Result(Rf): | dopa 0.58 |
| | N-maleyldopa 0.53 |
| | epinephrine 0.45 |
| | N-maleylepinephrine 0.52 |
| | norepinephrine 0.62 |
| | N-maleylnorepinephrine 0.74 |
| | dopamine 0.49 |
| | N-maleyldopamine 0.63 |

Thin layer chromatography (No. 2)

| Condition: | Carrier; cellulose |
|---|---|
| | Solvent; n-butanol-acetic acid-water(3:1:1) |
| | Temperature and time; 10–15° C, one hour |
| Result(Rf): | dopa 0.35 |
| | N-maleyldopa 0.74 |
| | epinephrine 0.35 |
| | N-maleylepinephrine 0.70 |
| | norepinephrine 0.28 |
| | N-maleylnorepinephrine 0.70 |
| | dopamine 0.38 |
| | N-maleyldopamine 0.83 |

The protected catecholamine is then conjugated with a carrier material such as proteins or polypeptides by Mannich's reaction. For example, several tens to several hundreds fold moles of the protected catecholamine to peptide or protein, such as BSA, is made to react as follows: Both reactants are dissolved in water, then an excess amount of formaldehyde and acetate buffer are added to the solution. The mixture is allowed to stand at room temperature or a slightly elevated temperature for a few or several days. After reaction, the mixture is dialyzed against, for example, diluted hydrochloric acid for a period of over 24 hours, and warmed. When the mixture is warmed in the presence of hydrochloric acid, the removal of the protective group such as maleyl as well as of formyl groups substituted to the amino group of the carrier material is accomplished. Then, the resulting mixture is dialyzed against water for 2 days and lyophilized. The lyophilized conjugate can be stocked. If antibodies are produced following to the synthesis of antigen, the aforementioned antigen treated with hydrochloric acid is dialyzed with a phosphate buffered saline (0.01M $KH_2PO_4$, 0.15M NaCl, pH 7.4) and suitably diluted with phosphate buffered saline and mixed with equal volume of Freund's adjuvant to prepare w/o type emulsion.

The hapten(catecholamine) was found to be conjugated to the carrier material at a ratio of 15-35 to one in the antigen (conjugate), which was detected by the color reaction originated from the catechol moiety with iron ions.

The physical properties of the antigen were determined by electrophoresis on cellulose-acetate and the conditions and results are summarized below.

Electrophoresis on cellulose acetate

| Condition: | Buffer solution;0.07M Veronal-sodium |
|---|---|
| | Veronal buffer |
| | solution,pH 8.6 |
| | Electric current and voltage; 2mA/cm,200-250volt |
| | Temperature and time; 10–15° C, 20 minutes |
| Result: | BSA +1cm |
| | epinephrine-BSA conjugate +1.5cm |
| | dopa-BSA conjugate +1.9cm |
| | dopamine-BSA conjugate +1.5cm |
| | norepinephrine-BSA conjugate +1.5cm |

The spots were detected by coloring with Ponceau 3R.

The antigen prepared as above can produce a very specific antibody to the antigen(catecholamines,conjugates), because all sensitive groups of the basic catecholamine remain in the conjugate as they are.

Catecholamine specific antibodies are produced in host animals and isolated from the sera by utilizing techniques well-known per se in the immunochemical art. For example, an emulsion of the conjugate (antigen) in Freund's adjuvant is injected to a host animal and after booster injections, the blood is collected. As for the host animals, use can be made of mammals such as cows, horses, sheep, goats, pigs, guinea pigs, rabbits, rats and the like. The serum collected may be treated with the carrier material used in the conjugation to remove the antibody to the carrier material. The serum was confirmed to be specific to the antigen(conjugate) by the Ouchterlony method (Handbook of Experimental Immunology 19.13 (1973)).

Isolation of the antibody from the serum is performed by, for example, passing through a column of DEAE-cellulose after dialysis. More precisely, the serum obtained above is dialyzed with urea solution then with phosphate buffer solution and passed through a DEAE-cellulose column. The gamma-globulin fraction ($\gamma$G-fraction) is collected by monitoring the absorbance at 280 nm. This fraction was confirmed as the antibody with high specificity to the antigen as well by Ouchterlony's method and the equilibrium dialysis method (F. Karush; Advance in Immunology, vol. 2, pages 1–40 (1962), etc.). After dialysis with water and lyophilization, the specific antibody may be stocked. The specific antibodies obtained by the present invention are useful for the measurement of catecholamines in various samples by immunoassay method such as radioimmunoassay.

The following examples illustrate the procedure of the preparation of antigen and antibody as well as the examination of specificities of antibodies.

EXAMPLE 1

Preparation of antigen and antibody of dopa.

In a suspension of 197mg of L-dopa and 2 ml of dimethylformamide, 200mg of maleic anhydride was dissolved. The reaction was performed in a water bath at 65°–70° C for about 30 minutes. Dimethylformamide was removed in vacuo and the residue was washed three times with 5ml of benzene to remove the unreacted maleic anhydride. The residue was dissolved in 2-3ml of cold water and the solution was neutralized by the dropwise addition of 0.01N cold solution of sodium hydroxide. The solution was lyophilized and the residue was dissolved in a little amount of methanol. Ethyl acetate was added to the solution and resulting precipitate was collected by centrifuging and dried in vacuo, so sodium salt of N-maleyldopa was obtained.

In 1ml of water, 33.9mg or 67.8mg of N-maleyldopa sodium salt and 100mg of BSA were dissolved. To the solution, 0.3ml of 3M sodium acetate and 1ml of 7.5% formaldehyde solution were added. After the substitution of nitrogen gas for air in the test tube with a ground stopper, the mixture was allowed to stand at room temperature (18°–23° C) in the dark for 5 days. Then the mixture was dialyzed with 0.01N hydrochloric acid and warmed up to 60° C for 3 hours. After the dialysis against the phosphate buffered saline for 2 days, the phosphate buffered saline was added to yield a final concentration of 10–20mg/ml of the conjugate. When the partial molar ratio between dopa portion and BSA portion of the conjugate was determined by a color reaction of iron chelete, it was found to be 16–24 mole dopa to one mole BSA.

The phosphate buffered saline solution of the conjugate was mixed with an equal volume of complete Freund's adjuvant to prepare a w/o type emulsion. The emulsion was intradermally injected to rabbit foot pads in the amount of 2–3mg of the antigen. After four weeks, phosphate buffered saline solution of the conjugate (1mg) was injected into the marginal vein of the rabbit ear. (This operation can be replaced by injecting subcutaneously the w/o emulsion of phosphate buffered saline solution of the conjugate (1mg) and incomplete Freund's adjuvant). One week after the booster injection, the rabbit were bled and the antisera were obtained.

The specificity of the antisera to the antigen was determined by the Ouchterlony method described below.

Agar was dissolved in phosphate buffered saline with warming to yield a final concentration of 1.2% and the solution was spread 2 mm in thickness on a glass plate. After cooling, 7 holes of 2mm diameter were made on the center and corners of a true hexagon with 5 mm side. In the center hole, the antiserum obtained above or diluted thereof to ½–⅛ with the phosphate buffered saline was filled. In the corner holes, the phosphate buffered saline solution of the conjugate (0.5–1.0mg/ml) and BSA were filled alternately. After standing overnight, the formation of precipitate was observed on both the conjugate and BSA. Therefore, an equal volume of BSA solution (1mg/ml) was added to the antiserum and the mixture was allowed to stand at 37° C for 1 hour, then at 4° C overnight. The resulted precipitates were removed by centrifuging. The resulting antiserum causes the precipitation with only the conjugate and not with BSA. This antiserum was then dialyzed with 6M urea solution for 15 hours followed with phosphate buffer (0.007M $NaH_2PO_4$, pH 6.3) for 2 days. The resulting solution was passed through a DEAE-cellulose column and the first fraction (gamma globulin fraction, γG-fraction) was collected with examining the absorbance at 280nm. When the fraction was examined by the Ouchterlony method, this fraction showed the specific precipitate to the antigen(conjugate). The γG-fraction was dialyzed with water and lyophilized for the stock.

EXAMPLE 2

Preparation of antigen and antibody of epinephrine.

In a suspension of 183.2mg of L-epinephrine and 5ml of methanol, 200mg of maleic anhydride was dissolved. After replacing the air with nitrogen gas, the reaction vessel was sealed and the solution was stirred in the dark at room temperature for one hour. After removing methanol, the mixture was neutralized by the same manner as in Example 1 and the unreacted epinephrine was removed by passing through a column of Dowex 50 WX-8 (Na type, 200 × 400 mesh, 0.9 × 7cm). Then the resulting solution of N-maleyl epinephrine sodium salt was lyophilized.

In 1 ml of water, the sodium salt (56.6mg or 84,9mg) and 100mg of BSA were dissolved. After the addition of 0.3ml of 3M sodium acetate and 1 ml of 7.5% formaldehyde solution, the mixture was treated by the same manner as in Example 1 and the phosphate buffered saline solution of epinephrine— BSA conjugate (10 – 20mg/ml) was obtained. The antigen was found to be a conjugate of 16 – 24 moles of epinephrine to one mole of BSA.

The hapten was bonded to BSA utilizing the ε-amino groups of BSA's lysine moieties, which was confirmed by amino acid analysis of epinephrine-BSA conjugate (T. P. King et al, J. Bio. Chem. 245 pages 6134 – 6148 (1970)). Epinephrine - BSA was dissolved in 6N hydrochloric acid and hydrolyzed at 110° C in a sealed tube for 24 hours. The data obtained by amino acid analyzer are shown in the following table. In the table, the value in the parentheses means the basic value.

| amino acid | control BSA analyzed by T.P.King et al. | BSA | BSA treated with formaldehyde | epinephrine-BSA |
| --- | --- | --- | --- | --- |
| Lys | 58 | (58) | 48 | 27 |
| His | 17 | 16 | 16 | 15 |
| Arg | 23 | 22 | (22) | (22) |
| Asp | 54 | (54) | (54) | (54) |
| Thr | 32 | 33 | 32 | 32 |
| Ser | 26 | 25 | 27 | 26 |
| Glu | 80 | 86 | 89 | 89 |
| Pro | 28 | 25 | 25 | 27 |
| Gly | 15 | 17 | 16 | 17 |
| Ala | 44 | 44 | 47 | 43 |
| Cys | 36 | 32 | 28 | 25 |
| Val | 35 | 34 | 32 | 32 |
| Met | 4 | 4 | 4 | 3 |
| Ile | 14 | 13 | 12 | 12 |
| Leu | 58 | 60 | 57 | 59 |
| Tyr | 19 | 20 | 3 | 11 |
| Phe | 26 | 28 | 27 | 25 |

Epinephrine specific antiserum was produced and γG-fraction was obtained by the same manner as in Example 1 using the phosphate buffered saline solution of the conjugate and complete Freund's adjuvant.

EXAMPLE 3

Preparation of antigen and antibody of norepinephrine.

In a suspension of 169mg of L-norepinephrine and 5 ml of methanol, 200mg of maleic anhydride was dissolved. The mixture was allowed to stand at room temperature for about 10 minutes and concentrated in vacuo. The residue was washed 2 times with 5ml of benzene, suspended in a mixture of methanol and water (1:1) and shaked enough with ethyl acetate. After centrifuging, the resulting precipitate was dried and a crystalline powder of N-maleylepinephrine was obtained. Analysis calculated for C 53.93, H 4.90, N 5.24, found C 53.81, H 5.02, N 5.16.

To a mixture of 80.3mg of N-maleylnorepinephrine and 100mg of BSA, 0.3ml of 1 m of sodium bicarbonate and 0.7 mg of water were added to the mixture of 3M sodium acetate and 1ml of 7.5% formaldehyde were added. Then the mixture was treated by the same manner as in Example 1, however, the reaction was performed for 3 days, and a phosphate buffered saline solution of the conjugate was obtained. 20–30 moles of norepinephrine was conjugated to one mole of BSA.

By the same manner as in Example 1, the antiserum of norepinephrine was produced and after removing the BSA-antibody, the γ-globuline fraction was obtained.

EXAMPLE 4

Preparation of antigen and antibody of dopamine

To a solution of 190mg of dopamine hydrochloride and 2ml of methanol, 0.4ml of triethylamine was dissolved and followed by the addition of 360mg of maleic anhydride. The solution was allowed to stand at room temperature for 10 minutes, methanol was removed in vacuo. The residue was washed twice with 5ml of benzene and after the addition of about 5ml of water, it was allowed to stand in the cold place, so slightly yellowish needles yielded. Analysis calculated for C 57.37,H 5.22,N 5.57, found C 56.95,H 5.34,N 5.55. In 0.3ml of 1M sodium bicarbonate solution, 75.3mg of N-maleyl-dopamine and 100mg of BSA were added. After the addition of 0.3ml of 3M sodium acetate and 1ml of 7.5% formaldehyde. The mixture was treated by the same manner as in Example 2 and the phosphate buffered saline solution of the conjugate was obtained. Dopamine and BSA were found to be conjugated in a ratio of 20–35 moles to one.

According to the same manner as in Example 1, the dopamine specific antibody and γG-fraction thereof was obtained.

EXAMPLE 5

Examination in the specificity of antisera

The specificity of antisera to the antigens was examined by the Ouchterlony method. Antisera were used after dealing with their carrier material to remove the antibodies to carrier material. As for the antigen of dopa, the conjugate of dopa with rabbit resum albumine(RSA) was used in addition to BSA-conjugate. The concentration of the antigen was 1mg/ml and the degree of the precipitate formation were indicated by the signs of +++, ++,+−, and −, in turn.

As shown in the table, each antiserum caused precipitation with the antigen thereof, however, did not cause or hardly caused precipitation with other antigens. It is concluded from the result that the antibody produced by the conjugate of this invention has high specificity in immunoreaction. On the other hand, as the antiserum to L-dopa-BSA conjugate caused precipitation with L-dopa-rabbit serum albumin conjugate(L-dopa-RSA), it is thought that the antibody detects the hapten with selectivity.

| antigen | antiserum to L-dopa-BSA | antiserum to epine-phrine-BSA | antiserum to dopamine-BSA | antiserum to norepi-nephrine |
|---|---|---|---|---|
| L-dopa-BSA | +++ | − | − | − |
| L-dopa-RSA | +++ | − | − | − |
| epinephrine-BSA | − | +++ | +− | +− |
| dopamine-BSA | +− | +− | ++ | +− |
| norepinephrine-BSA | +− | +− | +− | ++ |

EXAMPLE 6

Examination in the specificity of the epinephrine antibodies by the equilibrium dialysis method.

The γ-globulin fraction obtained in Example 2 was dialyzed against the phosphate buffered saline and a solution of the final concentration of 0.94mg/ml was performed prepared. The γ-globulin solution was used as the antibody solution in this method. To the phosphate buffered saline used in this procedure, 0.01% of sodium metabisufite($Na_2S_2O_5$) and 0.015% ethylenediaminetetraacetic acid disodium salt were added.

An equilibrium dialysis apparatus of 2ml capacity was used and 500μl of the antibody solution was poured into one of a pair cell(cell A) and into another cell(cell B), 10μl of the phosphate buffered saline solution of DL-epinephrine labelled with tritium($^3H$) in a concentration of $3.4\times10^{-5}M$ and 490μl of phosphate buffered saline were introduced. They were shaked at 25° C to reach equilibrium and then radioactivity of each solution were counted. The difference of each counts was calculated and made as the standard.

Then, 500μl of γ-globulin solution was put in cell A, and in cell B were introduced 10μl of a solution of the concentration of $3.4\times10^{-3}M$ of epinephrine or one of other catecholamine or analogue compounds, 10μl of a phosphate buffered saline solution of $^3H$-epinephrine ($3.4\times10^{-5}M$) and 480μl of phosphate buffered saline. The solutions were shaked by the same manner as above and after equilibrium, the radioactivity of each solution were counted. The difference was calculated and the relative bindings were calculated from the standard.

| compound | relative binding (%) |
|---|---|
| — | 100 |
| L-epinephrine | 0 |
| L-dopa | 90.7 |
| dopamine | 88.0 |
| L-norepinephrine | 54.8 |
| DL-methanephrine | 81.7 |
| DL-normetanephrine | 97.2 |
| 3,4-dihydroxyphenylacetic acid | 83.8 |
| 4-hydroxy-3-methoxyphenylacetic acid | 91.7 |
| L-isoproterenol | 72.9 |

[3]H-epinephrine was DL-epinephrine and the concentration of the antibody used was $5.5\times10^{-6}M$.

What is claimed is:

1. An antigen prepared by a process, consisting essentially of: reacting a catecholamine with a protein or polypeptide carrier and an aldehyde via the Mannich reaction such that said catecholamine is attached through a substituted or unsubstituted methylene linkage to an amine group of said carrier at an unsubstituted position on the phenyl nucleus of said catecholamine.

2. The antigen of claim 1, wherein the catecholamine is selected from the group consisting of epinephrine, norepinephrine, dopamine and dopa.

3. The antigen of claim 1, wherein the protein is bovine serum albumin.

4. A process for producing a catecholamine specific antibody, which comprises: injecting an antigen prepared by the process of claim 1 into a host animal; withdrawing blood from said injected animal; and isolating said catecholamine specific antibodies.

5. The process of claim 4, wherein the host animal is selected from the group consisting of cows, horses, sheep, goats, pigs, guinea pigs, rats and rabbits.

6. The catecholamine specific antibody produced by a process of claim 4.